(12) United States Patent
Kim et al.

(10) Patent No.: US 11,781,992 B2
(45) Date of Patent: Oct. 10, 2023

(54) TEST STRIP FOR DETECTING MICROALBUMIN IN URINE WITH HIGH SENSITIVITY

(71) Applicant: CHUNGDO PHARM. CO., LTD, Chuncheon-si (KR)

(72) Inventors: Sung Jin Kim, Seoul (KR); Abeje Abebayehu Silte, Chuncheon-si (KR); Hyun Ah Kim, Chuncheon-si (KR)

(73) Assignee: CHUNGDO PHARM. CO., LTD, Chuncheon-si (KR)

( * ) Notice: Subject to any disclaimer, the term of this patent is extended or adjusted under 35 U.S.C. 154(b) by 495 days.

(21) Appl. No.: 17/014,380

(22) Filed: Sep. 8, 2020

(65) Prior Publication Data
US 2021/0096080 A1    Apr. 1, 2021

(30) Foreign Application Priority Data

Sep. 30, 2019    (KR) .......... 10-2019-0120891

(51) Int. Cl.
*G01N 21/78*    (2006.01)
*G01N 33/68*    (2006.01)
*G01N 21/77*    (2006.01)

(52) U.S. Cl.
CPC ............. *G01N 21/78* (2013.01); *G01N 33/68* (2013.01); *G01N 2021/7759* (2013.01); *G01N 2333/76* (2013.01)

(58) Field of Classification Search
CPC ........... G01N 2021/7759; G01N 21/78; G01N 2333/76; G01N 33/523; G01N 33/68; G01N 33/6827
See application file for complete search history.

(56) References Cited

U.S. PATENT DOCUMENTS 5,187,104 A    2/1993    Corey et al.

FOREIGN PATENT DOCUMENTS

| CN | 103278648 A | 9/2013 | |
| EP | 670493 A2 * | 9/1995 | ............. G01N 33/52 |
| JP | 3955911 B2 | 8/2007 | |
| KR | 10-2013-0088623 A | 8/2013 | |
| KR | 10-2015-0141952 A | 12/2015 | |

OTHER PUBLICATIONS

Office Action dated Sep. 16, 2020 by the Korean Patent Office in Korean Application No. 10-2019-0120891.

* cited by examiner

*Primary Examiner* — Jennifer Wecker
(74) *Attorney, Agent, or Firm* — Sughrue Mion, PLLC

(57) ABSTRACT

Disclosed is a test strip for detecting microalbumin in urine, and more particularly a test strip for detecting microalbumin in urine that contains a synthetic albumin indicator, a buffer solution, a surfactant and a polymer (sensitizer) and thus exhibits high sensitivity. The albumin detection test strip has accuracy sufficient to enable clear observation of color change from colorless to blue through the albumin indicator, and improves the detection limit (increases sensitivity) to thereby enable detection of microalbuminuria at a concentration of 20 mg/L or less. The albumin test detection strip contains a surfactant and a polymer in addition to a synthetic albumin indicator, thereby incorporating separate first and second processes into a single process and having effects of reducing costs, improving processing convenience, and increasing solubility and miscibility.

8 Claims, 4 Drawing Sheets
(2 of 4 Drawing Sheet(s) Filed in Color)

| | In order of concentration (mg/L) <20 / 50 / 100 / 150 / 200 |
|---|---|
| 1) | |
| 2) | |
| 3) | |

TEST STRIP FOR DETECTING MICROALBUMIN IN URINE WITH HIGH SENSITIVITY

CROSS REFERENCE TO RELATED APPLICATIONS

This application claims priority from Korean Patent Application No. 10-2019-0120891, filed on Sep. 30, 2019, the entire disclosure of which is incorporated herein by reference.

BACKGROUND OF THE INVENTION

Field of the Invention

The present invention relates to a test strip for detecting microalbumin in urine, and more particularly to a test strip for detecting microalbumin in urine that contains an albumin indicator, a buffer solution, a surfactant and a polymer (sensitizer), and thus exhibits high sensitivity.

Description of the Related Art

Albumin is a plasma protein that constitutes more than half of all proteins and is present in the largest amount. Albumin plays important roles in preventing the outflow of body fluids by retaining body fluids in the blood vessels and in delivering various compounds such as bilirubin, fatty acids, cortisol, thyroxine, and drugs such as sulfonamides and barbiturates. Deficiency of albumin causes abnormal accumulation of intestinal fluid and edema, and limits the transport of body fluids due to decreased osmotic function. Therefore, it is clinically important to examine serum albumin deficiency.

Normal human urine albumin is generally 20 mg/L or less. An abnormal excretion rate ranging from 20 to 200 mg/L of albumin in urine and from 30 to 300 mg/L of creatinine in urine means "microalbuminuria". Microalbuminuria is an indicator of endothelial cell dysfunction and cardiovascular morbidity, and is very important in diagnosing various pathological diseases affecting the kidneys, circulatory system and central nervous system. Microalbuminuria in patients having a high risk of kidney disease indicates high blood pressure and diabetes. These symptoms of kidney disease and damage may lead to kidney failure. In addition, microalbuminuria is generally determined to be an early symptom of diabetic nephropathy patients.

A method of detecting microalbumin in urine may be realized through various colorimetry-based methods for measuring color change through formation of a complex between microalbumin and an indicator. There are a variety of methods such as test strips, immunofluorescence, enzyme immunoassay, radioimmunoassay, and immunoassay. Among them, the test strip (dipstick dry chemical method) using a change in color by the combination of microalbumin with an indicator in urine is the simplest method. Test strips are produced by impregnating a support with a reagent that reacts with microalbumin, followed by drying, and the indicator includes 2-(4'-hydroxyazobenzene) benzoic acid (HABA), bromocresol green, bromocresol blue, bromophenol blue (BPB), tetrabromophenol blue (TBPB), bis(3,3"-diiodo-4',4"-dihydroxy-5',5"-dinitrophenyl)-3,4,5,6-tetrabromosulfonphthalein (DIDNTB) and the like.

However, the conventional method using an alkaline triphenyl methane derivative indicator has a problem in terms of color expression (accuracy) and detection limits in which microalbumin in an amount of 20 mg/L or less is not detected, thus making it impossible to detect slight changes in color by about 10 to about 30 mg/L of a trace amount of protein (microalbuminuria) in urine. Therefore, there is a need for the development of a method to detect microalbuminuria with a low detection limit (high sensitivity) in terms of early diagnosis of diabetic nephropathy patients and predicting renal failure while exhibiting relatively clear color change.

PRIOR ART

Patent Document

Korean Patent Application No. 10-2015-7027368 (publication date: Mar. 11, 2014) relates to a rapid test for urine albumin and urine creatinine, and discloses an immunochromatographic system for measuring albumin and creatinine in a urine sample and a reader that detects signals from the test cassette, calculates, and displays the results for albumin concentration, creatinine concentration, and albumin-creatinine ratio.

SUMMARY OF THE INVENTION

Therefore, the present invention has been made in order to solve the drawbacks with the prior art, and it is an object of the present invention to provide a strip for a microalbumin detection test that contains a synthetic albumin indicator, a buffer, Triton X-100 and polypropylene glycol, and thus exhibits an improved detection limit.

In accordance with the present invention, the above and other objects can be accomplished by the provision of a method for producing an albumin detection test substrate including (a) adding a surfactant, a sensitizer and an albumin indicator to a buffer solution to prepare an impregnation solution, and (b) impregnating a detection substrate with the solution and drying the detection substrate, wherein the buffer solution is prepared by mixing ethanol, citric acid and trisodium citrate.

Preferably, the buffer solution may be prepared by slowly mixing 20 to 40 parts by weight of citric acid and 10 to 30 parts by weight of trisodium citrate based on 100 parts by weight of ethanol.

Preferably, the surfactant may be Triton X-100.

Preferably, the sensitizer may be polypropylene glycol.

Preferably, the method may further include slowly mixing 20 to 40 parts by weight of citric acid, and 10 to 30 parts by weight of trisodium citrate, based on 100 parts by weight of ethanol, to prepare the buffer solution, mixing the buffer solution with 0.1 to 2 parts by weight of Triton X-100, 4 to 6 parts by weight of polypropylene glycol, and 2 to 3 parts by weight of the albumin indicator to prepare an impregnation solution, and impregnating the substrate with the impregnation solution and drying the substrate in an oven.

Preferably, the albumin indicator may be 5',5"-dinitro-3',3",3,4,5,6-hexabromophenolsulfonephthalein.

Preferably, the detection substrate may be paper, nonwoven fabric or sponge.

In accordance with another aspect of the present invention, provided is a method of producing a urine albumin detection test strip, including cutting the albumin detection test substrate produced above and then attaching the albumin detection substrate to a PVC sheet support.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and other advantages of the present invention will be more clearly understood from the following detailed description taken in conjunction with the accompanying drawings, in which.

DETAILED DESCRIPTION OF THE INVENTION

Figure 1A:
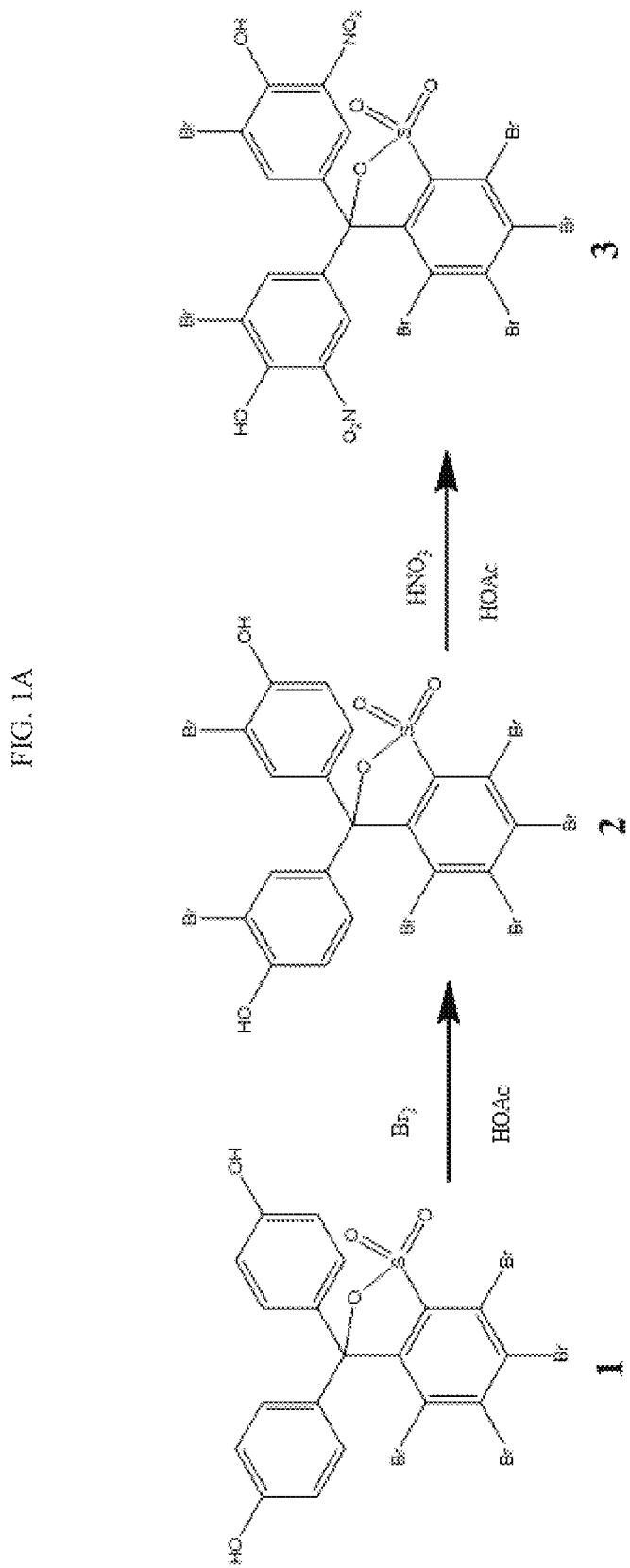
FIG. 1A shows a chemical reaction process from 3,4,5,6-tetrabromophenolsulfonephthalein (compound 1 in FIG. 1A) to an albumin indicator of the present invention (compound 3 in FIG. 1A)

Microalbuminuria refers to an abnormal excretion rate corresponding to a urine albumin range of 20 to 200 mg/L and a urine creatinine range of 30 to 300 mg/L. Microalbuminuria is an indicator of endothelial cell dysfunction and cardiovascular morbidity, which is very important in diagnosing various pathological diseases that affect the kidneys and the circulatory and central nervous systems. However, a conventional method using an alkaline triphenyl methane derivative indicator has problems associated with the accuracy of color expression and the detection limit, in which microalbumin in amounts of 20 mg/L or less is not detected, thus making it impossible to detect a slight change in color by a trace amount of protein (microalbuminuria) of about 10 to 30 mg/l in urine.

Accordingly, in the present invention, an albumin test strip that enables accurate, convenient, and quick measurement within one minute was produced by developing a semi-quantitative dipstick test method using a test strip (dry chemistry method) that can detect urine inexpensively and conveniently, and adding an albumin indicator to cause a color change in the presence of albumin.

Specifically, the present invention provides a method for producing an albumin detection test substrate including adding a surfactant, a sensitizer and an albumin indicator to a buffer solution to prepare an impregnation solution, then impregnating paper with the solution and drying the paper, wherein the buffer solution is prepared by mixing ethanol, citric acid and trisodium citrate.

Meanwhile, in the present invention, the buffer solution is preferably prepared by slowly mixing 20 to 40 parts by weight of citric acid and mixing 10 to 30 parts by weight of trisodium citrate based on 100 parts by weight of ethanol.

The method for preparing the albumin detection test substrate according to the present invention will be described in detail. The method includes: slowly mixing 20 to 40 parts by weight of citric acid, and mixing 10 to 30 parts by weight of trisodium citrate, based on 100 parts by weight of ethanol to prepare a buffer solution (a); mixing the buffer solution of step (a) with 0.1 to 2 parts by weight of Triton X-100, 4 to 6 parts by weight of polypropylene glycol, and 2 to 3 parts by weight of an albumin indicator to prepare an impregnation solution (b); and impregnating paper with the impregnation solution of step (b) and drying the paper in an oven (c).

In addition, the present invention provides a method of producing a urine albumin detection test strip, including cutting a urine albumin detection test substrate and then attaching the test substrate to a PVC sheet support.

In the present invention, in order to produce the albumin detection test strip (dry test strip), a buffer solution, a surfactant, a polymer (sensitizer) and an albumin indicator are dissolved in a solvent, and then paper is impregnated with the solution to produce the test strip. As a result, all substances are not released and contained in paper, so that an optimal state in which the indicator reacts with the reactant can be maintained. Also, microalbumin can also be detected using the buffer solution developed in the present invention.

In the present invention, the term "buffer solution" functions to offer a constant-pH environment for the reaction of the indicator and thereby to help prevent the indicator reaction from being affected by the pH of urine. Since the pH environment varies depending on the type and concentration of the buffer, it is important to adjust an appropriate pH at which the indicator can act and react. It is known that a pH of 1.5 to 4.5, preferably a pH of 2.0 to 3.0, and most preferably a pH of 2.5 is suitable for the color development of the indicator for the detection of albumin.

The buffer that activates reaction and lowers the pH through electron donation in the solution is preferably citric acid, malonic acid, sulfosalicylic acid, phosphoric acid or the like. The buffer solution was prepared by mixing 20 to 40 parts by weight of citric acid and 10 to 30 parts by weight of trisodium citrate based on 100 parts by weight of a solvent so that color development was appropriate even in the microalbumin content.

In the present invention, the surfactant functions to keep the color change of the color indicator uniform. In addition, the surfactant stabilizes the color formation of the indicator to thereby increase reactivity and improve accuracy. By changing the concentration and type of surfactant, positive and negative color changes were detected to determine the effect of additives on the test strip. Examples of reagent mainly used as the surfactant include sodium dodecyl sulfate (SDS), Triton X-100, dodecylbenzenesulfonic acid (DBS), dioctyl sulfosuccinate, glycerol and the like. In the present invention, it was found that Triton X-100 was suitable as the surfactant for color development of the albumin test strip, and Triton X-100 was used in an amount of 0.1 to 2.0 parts by weight.

In the present invention, the sensitizer refers to a material that maintains color development and negative color during an effective period to improve stability, and means a polymer that improves color formation kinetics and reactivity with the albumin indicator, and has a molecular weight of 200 to 25,000. The sensitizers (polymers) that are mainly used preferably include polyethylene glycol, polypropylene glycol, polycarbonate, polyvinyl ether and the like, and more preferably polyethylene glycol or polypropylene glycol. The concentration of the sensitizer is not particularly limited, and is preferably 3 to 10 parts by weight, more preferably 4 to 6 parts by weight.

In the present invention, the polymer (sensitizer) is useful for both water-soluble and water-insoluble polypropylene glycol, and the polypropylene glycol preferably has a molecular weight of 400 to 10,000, and most preferably 1,000 to 2,000. In the examples of the present invention, water-soluble polypropylene glycol having an average molecular weight of 400 was determined to be useful, and polypropylene glycol was used in an amount of 4 to 6 parts by weight. This results in an increased color response range and improved reaction kinetics with albumin. In conclusion, the albumin test detection strip of the present invention includes a synthetic albumin indicator and polypropylene glycol, thereby improving sensitivity and reaction speed as well as resolution with albumin in urine.

Meanwhile, in the present invention, the albumin indicator is preferably 5',5"-dinitro-3',3",3,4,5,6-hexabromophenolsulfonephthalein.

The 5',5"-dinitro-3',3",3,4,5,6-hexabromophenolsulfonephthalein is preferably prepared through the following process.

5',5"-dinitro-3',3",3,4,5,6-hexabromophenolsulfonephthalein may be obtained as a pure yellow powder through the process including: preparing a solution containing 9 to 11 parts by weight of 3,4,5,6-tetrabromophenolsulfonephthalein in 100 parts by weight of acetic acid (HOAc) at room temperature under an inert gas atmosphere (a); dropwise treating the solution prepared in step (a) with a solution containing 4 to 5 parts by weight of bromine in 20 parts by weight of acetic acid for 10 minutes, followed by stirring for 48 hours (b); collecting a solid isolated from the stirred mixture by filtration, washing the solid with acetic acid (HOAc) and drying the same in a vacuum to obtain 3',3",3,4,5,6-hexabromophenolsulfone-phthalein (c); recrystallizing the prepared 3',3",3,4,5,6-hexabromophenolsulfone-phthalein in boiling acetic acid to obtain a compound as a pale yellow powder (d); preparing a solution containing 5 to 6 parts by weight of the compound of step (d) in 100 parts by weight of anhydrous acetonitrile (CH3CN) under ambient temperature and an inert gas atmosphere (e); treating the solution prepared in step (e) with an acetic acid catalyst and dropwise treating 100 parts by weight of the resulting solution with 0 to 1 part by weight of a 90% solution of sodium nitrite, followed by stirring for 96 hours (f); collecting a solid from the stirred mixture by filtration and then washing the same with acetonitrile (CH3CN), and drying the same under vacuum (g).

Meanwhile, according to the following experiment, the albumin detection test strip of the present invention was found to change from bright sky blue to dark sky blue depending on the concentration, thereby enabling microalbumin detection. This overcomes the drawbacks of test papers in the conventional process. Conventional test papers had a negative color of dark yellow and thus changed from yellow to yellowish green to green depending on the albumin concentration in the sample when albumin and an octahalosulfophthalein indicator react with each other. However, in the case of the most commonly tested body fluid (yellow urine), there are problems in that it is impossible to distinguish a small change in color by about 10 to 30 mg/L of microalbumin in urine based on the color change and in that sensitivity is poor. However, in the present invention, this problem has been solved.

Compared with the chemical reaction of DIDTNB with the general bromine substitution reaction, the present invention is differentiated therefrom in that it is a nitration reaction using acetonitrile (CH$_3$CN). The principle of the nitration reaction will be described in detail. The nitro or nitroso group adjacent to the hydroxy group at positions 4' and 4" improves the reactivity of the hydroxy group and resonance stability through charge distribution, and increases acidity at positions 4' and 4" to thereby decrease the pKa and improve the sensitivity of the albumin indicator. Through this, the albumin indicator of the present invention can improve the sensitivity of the urine albumin reaction and cause change from sky blue to blue at a low concentration of albumin, thereby enabling microalbumin detection.

In addition, the albumin test detection strip of the present invention can incorporate separate first and second processes into a single process by mixing a buffer solution, Triton X-100, and water-insoluble polypropylene glycol in a single process, thus exhibiting effects of reducing costs, improving processing convenience, and increasing solubility and miscibility.

Meanwhile, in the present invention, the term "substrate" refers to an object on which the indicator of the present invention is loaded, and examples thereof include paper, nonwoven fabric, sponge and the like. The substrate of the present invention detects albumin in a sample when it comes into contact with the sample containing albumin and visually displays the same.

Hereinafter, the present invention will be described in more detail with reference to the following examples and experimental examples. The scope of the present invention is not limited to the examples and experimental examples, and includes modifications of the technical concept equivalent thereto.

Example 1

Preparation of Synthetic Albumin Indicator for Urine Test Paper

In this example, a synthetic albumin indicator for urine test paper was prepared as follows.

First, a solution of 7.5 mmol (10.06 g) of 3,4,5,6-tetrabromophenolsulfonephthalein (Compound 1) in 100 ml of acetic acid (HOAc) was prepared at room temperature under inert gas atmospheric conditions. A solution of 15 mmol (4.8 g) of bromine in 20 ml of acetic acid (HOAc) was dropwise added to the prepared solution for 10 minutes, followed by stirring for 48 hours, and the solid isolated from the reaction mixture was collected through filtration, washed with acetic acid (HOAc) and dried in a vacuum to prepare 3',3",3,4,5,6-hexabromophenolsulfone-phthalein (Compound 2). The compound 2 was recrystallized in boiling acetic acid (boiling HOAc) to obtain pure compound 2 (5.79 g, 683%) as a pale yellow powder. Spectroscopic results of Compound 2 were as follows; $^1$H NMR (DMSO-d$_6$), 7.11 (d, J=8.7 Hz, 2H), 7.31 (dd, J$_1$=8.7 Hz, J$_2$=2.4 Hz, 2H), 7.59 (d, J=2.4 Hz, 2H), 8.03 (s, 2H). IR (KBr) cm$^{-1}$ 1192, 1227, 1295, 1340, 1360, 1416, 1497, 1605, 1703, 3435.

A solution of Compound 2 in 100 ml of anhydrous acetonitrile (CH$_3$CN) was prepared at room temperature under an inert gas atmosphere. The prepared solution was treated with a catalyst of acetic acid (HOAc). A 90% solution of sodium nitrite (0.56 g, 48 mmol) was dropwise added to the treated solution, followed by stirring for 96 hours (4 days). The solid isolated from the reaction mixture was collected by filtration, washed with acetonitrile (CH$_3$CN), and dried in a vacuum to prepare compound 3, 5',5"-dinitro-3',3",3,4,5,6-hexabromophenolsulfonephthalein) (4.03 g, 64%, melting point of 267 to 269° C.) as a pure yellow powder.

FIG. 1A shows the chemical reaction process (Compounds 1 to 3) from Compound 1 (3,4,5,6-tetrabromophenolsulfonephthalein) to the albumin indicator of the present invention. For comparison, FIG. 1B shows a general bromine substitution reaction process (Compounds A to C) from 3,4,5,6-tetrabromophenolsulfonephthalein and a chemical reaction process (Compounds A to E) to DIDTNB therefrom.

Figure 1B:
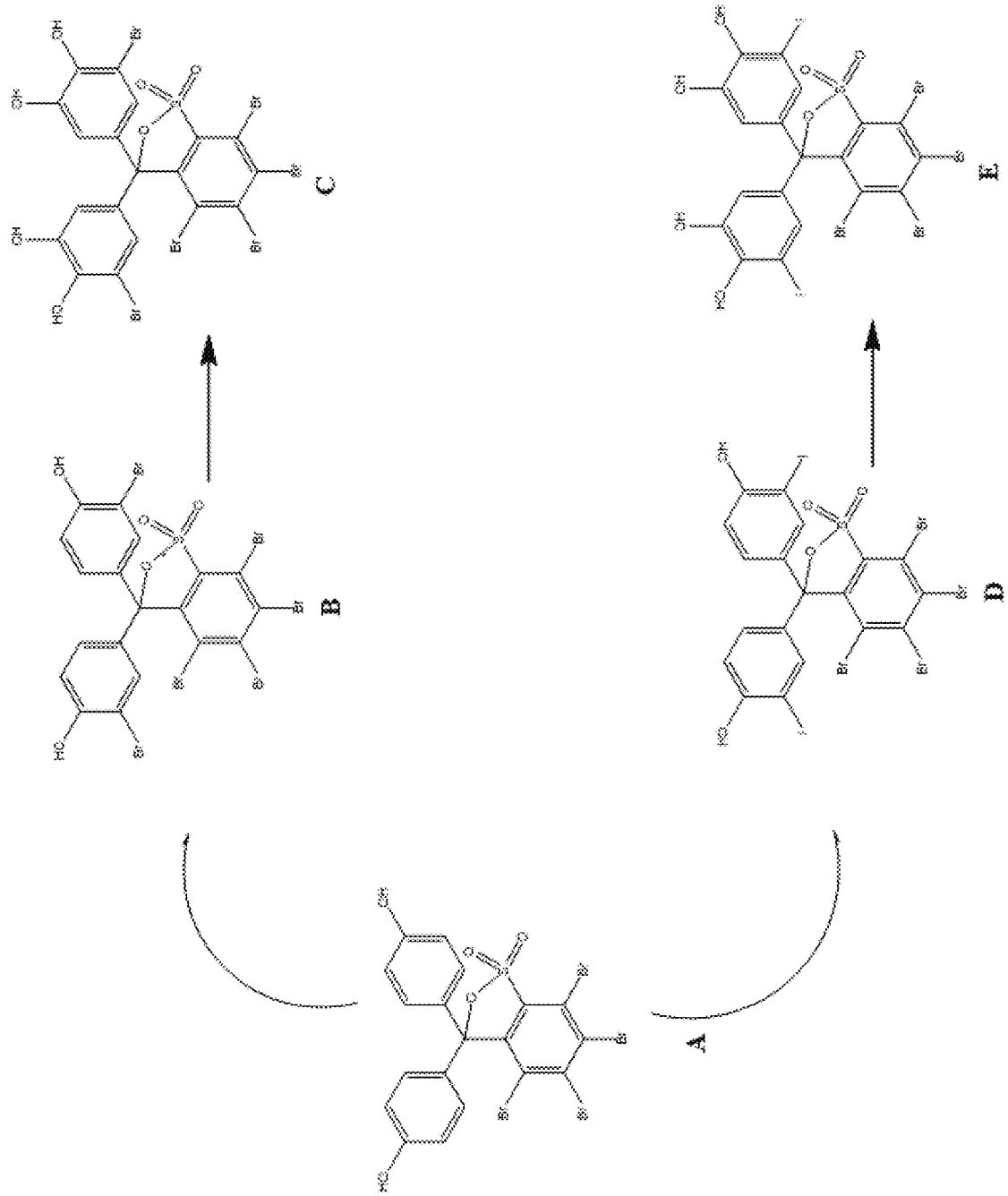
FIG. 1B shows a general bromine substitution reaction process (A to C) from 3,4,5,6-tetrabromophenolsulfonephthalein (compound A in FIG. 1B) and a chemical reaction process (A to E) to DIDTNB therefrom.

In FIG. 1B, in Compounds B and C involved in the bromine substitution reaction, substitution may occur at the position 3',3",3,4,5,5',5" or 6 with halogens, alkyl groups or protons (H) in order to obtain a desired compound. Compared thereto, FIG. 1A shows a chemical reaction process to the albumin indicator of the present invention, and Compounds 2 and 3 are involved in the nitration reaction. The principle of this reaction is described in detail. The nitro or nitroso group adjacent to the hydroxy group at positions 4' and 4" improves the reactivity of the hydroxy group and resonance stability through charge distribution, and increases acidity at positions 4' and 4" to decrease the pKa and thereby improve the sensitivity of the albumin indicator. Through this, the albumin indicator of the present invention can improve the sensitivity of a urine albumin reaction and cause a change from light blue to blue at a low concentration of albumin, thereby enabling microalbumin detection.

Meanwhile, in the chemical reaction process (FIG. 1B, Compounds A to E) of DIDTNB for comparison, Compound A was reacted with iodine monochloride (ICl) in acetic acid to produce 3,4,5,6-tetrabromohenolsulfonephthalein as Compound D, to thereby obtain DIDTNB as Compound E.

In conclusion, compared to the chemical reaction of DIDTNB and the general bromine substitution reaction, the albumin indicator of the present invention has effects of improving the reaction sensitivity of the albumin indicator through the nitration reaction using acetonitrile ($CH_3CN$) and detecting albumin at a low concentration.

Example 2

Process of Producing Albumin Detection Test Strip Using Albumin Indicator for Urine Test Paper of Example 1

In this example, the albumin indicator (Compound 3) for the urine test strip of Example 1, a buffer solution, a surfactant, and a polymer (sensitizer) were impregnated into a Whatman test paper to produce a test paper, and then a detection test strip (dry test strip) was prepared using the same.

1) Test Paper Production 28 parts by weight of citric acid was slowly mixed with 100 parts by weight of ethanol, and 21 parts by weight of trisodium citrate was mixed therewith to prepare a buffer solution (also referred to as a loading solution). 1 part by weight of Triton X-100 as a surfactant was mixed with the solution to improve the solubility, and 5 parts by weight of polypropylene glycol as a polymer (sensitizer) was mixed with 2.5 parts by weight of the albumin indicator (Compound 3) synthesized above to prepare a single impregnation solution. After preparing the single impregnation solution, a Whatman paper was impregnated with the impregnation solution such that the compound was sufficiently absorbed in the Whatman paper, and was then dried in an oven at 60° C. for 30 minutes to produce test paper.

2) Test Strip Production

Figure 2:
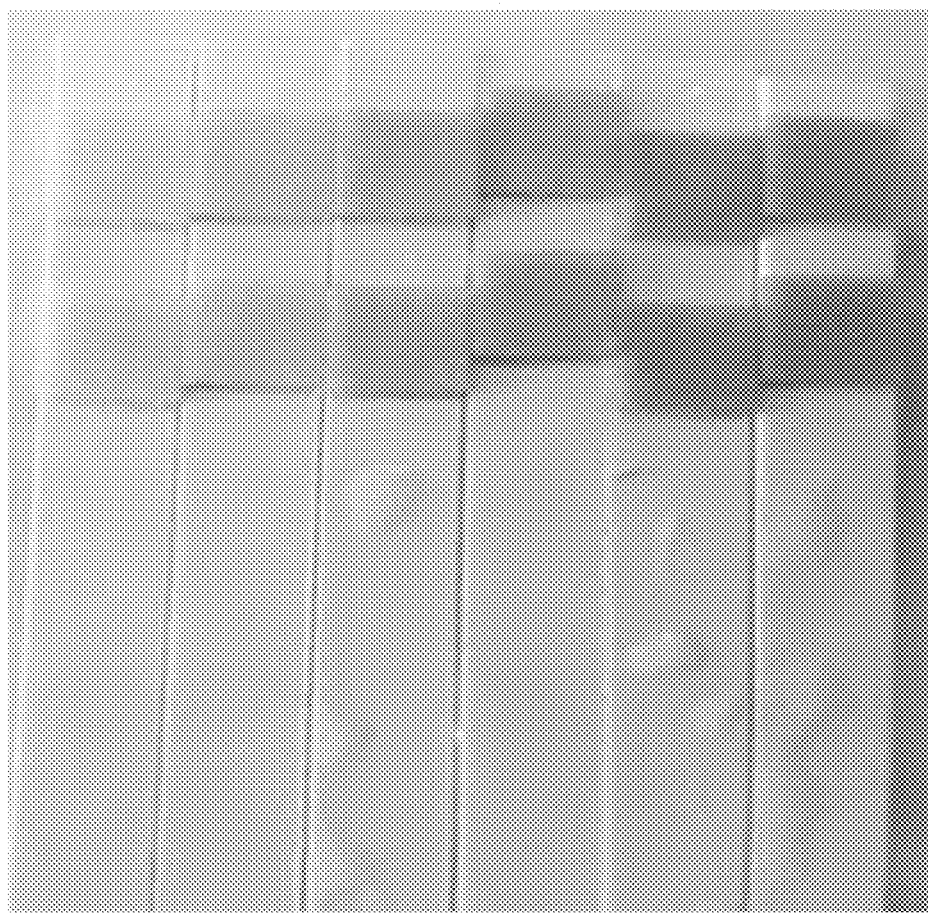
FIG. 2 is an image showing an albumin detection test strip according to the present invention.
Figures 3, 4:
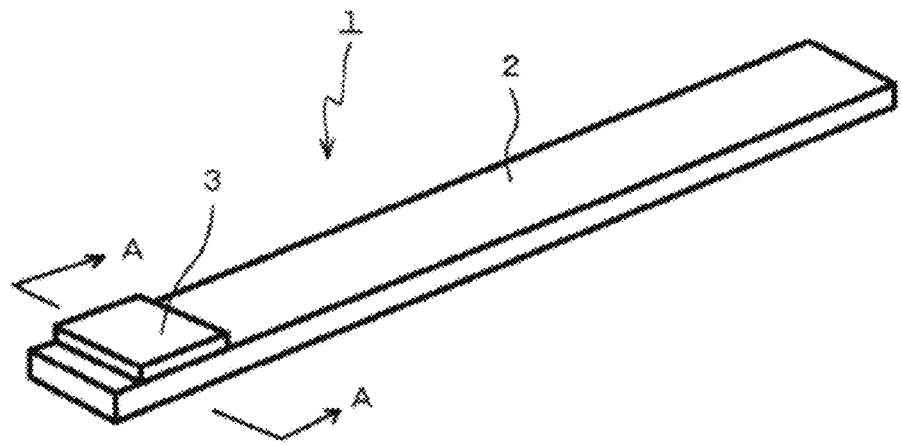
FIG. 3 is an image showing an albumin detection test strip according to the present invention, wherein 1 shows an albumin detection test paper, 2 shows a support, and 3 shows a paper impregnated with an albumin detection reagent.
FIG. 4 is an image showing detection tests using a test strip produced through a single process of the albumin indicator (Compound 3) according to the present invention, a test strip produced through primary and secondary processes of the albumin indicator (Compound 3), and DIDTNB.

As described above, after the production of the test paper, the test paper was cut to an appropriate size and attached to a long rod-shaped PVC sheet support to produce a test strip. The rod-shaped PVC support used herein was a non-reactive substance that does not react with any components of urine. The albumin detection test strip using the same was found to change from bright sky blue (20 mg/L or less) to dark sky blue (200 mg/L) as shown in FIG. 2. The test strip and the configuration thereof are shown in FIG. 3.

Experimental Example 1

Test for Albumin Detection Test Strip of Present Invention

In this experimental example, the detection efficacy of the albumin detection test strip using the albumin indicator (Compound 3) of the present invention was tested. DIDTNB used in the experiment for comparison of detection efficacy was bis(3',3"-diiodo-4',4"-dihydroxy-5',5"-dinitrophenyl)-3, 4,5,6-tetrabromosulfonphthalein (Cas Number 11NOVO49, bought from UKChem, UK).

As shown in FIG. 3, the albumin detection test strip produced through a single process using the albumin indicator (Compound 3) of the present invention was found to change from bright sky blue to dark sky blue depending on the concentration to thus enable detection of microalbumin. In the case of conventional DIDTNB, the negative color is dark yellow, so it is difficult to detect microalbumin due to the problem of changing from yellow to yellowish green to green when albumin reacts with the indicator.

In addition, the albumin test detection strip of the present invention can reduce costs, improve process convenience, and increase the solubility and miscibility by mixing a buffer solution, Triton X-100, and water-insoluble polypropylene glycol in a single process. Through this, the albumin detection test strip of the present invention can accurately and clearly detect microalbumin at a concentration (20 mg/L or less) lower than the albumin concentration detectable by conventional methods.

As apparent from the foregoing, the albumin detection test strip according to the present invention has accuracy sufficient to provide clear observation of color change from colorless to blue through an albumin indicator, and lowers the detection limits (increases sensitivity) to enable detection of microalbuminuria at a concentration of 20 mg/L or less.

In addition, the albumin detection test strip of the present invention has effects of reducing costs, providing process convenience, and improving solubility and miscibility by adding a surfactant and a polymer to an albumin indicator to incorporate the first and second processes into a single process.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for producing an albumin detection test substrate comprising:
   (a) a single process of adding a surfactant, a sensitizer and an albumin indicator to a buffer solution to prepare an impregnation solution; and
   (b) impregnating a substrate with the impregnation solution and drying the substrate to obtain the albumin detection test substrate,
   wherein the buffer solution is prepared by mixing ethanol, citric acid and trisodium citrate,
   wherein the albumin indicator is 5',5"-dinitro-3',3",3,4,5, 6-hexabromophenolsulfonephthalein,
   wherein the sensitizer is polypropylene glycol, and wherein the buffer solution is prepared by slowly mixing 20 to 40 parts by weight of citric acid and 10 to 30 parts by weight of trisodium citrate based on 100 parts by weight of ethanol.

2. The method according to claim 1, wherein the surfactant is Triton X-100.

3. The method according to claim 1, wherein the sensitizer is polypropylene glycol.

4. The method according to claim 1, further comprising:
prior to the step (a), slowly mixing 20 to 40 parts by weight of citric acid, and 10 to 30 parts by weight of trisodium citrate, based on 100 parts by weight of ethanol, to prepare the buffer solution;
wherein the step (a) is conducted by mixing the buffer solution with 0.1 to 2 parts by weight of Triton X-100, 4 to 6 parts by weight of polypropylene glycol, and 2 to 3 parts by weight of the albumin indicator to prepare the impregnation solution, and
wherein in the step (b), the drying the substrate is conducted using an oven.

5. The method according to claim 1, wherein the substrate is paper, nonwoven fabric or sponge.

6. A method of producing a urine albumin detection test strip, comprising cutting the albumin detection test substrate produced according to the method of claim 1 and then attaching the albumin detection test substrate to a PVC sheet support.

7. A method of detecting albumin in a urine sample, comprising
contacting the urine sample with the albumin detection test substrate according to claim 1.

8. The method of claim 7, wherein a concentration of albumin in the urine sample is 20 mg/L or less.

* * * * *